United States Patent
Hellenbrand

(10) Patent No.: US 10,839,047 B2
(45) Date of Patent: Nov. 17, 2020

(54) AUTOMATIC PICKING MACHINE FOR FILLING A TRANSPORT CONTAINER

(71) Applicant: Becton Dickinson Rowa Germany GmbH, Kelberg (DE)

(72) Inventor: Christoph Hellenbrand, Kelberg (DE)

(73) Assignee: BECTON DICKINSON ROWA GERMANY GMBH, Kelberg (DE)

( * ) Notice: Subject to any disclaimer, the term of this patent is extended or adjusted under 35 U.S.C. 154(b) by 0 days.

(21) Appl. No.: 16/730,846

(22) Filed: Dec. 30, 2019

(65) Prior Publication Data
US 2020/0135322 A1    Apr. 30, 2020

Related U.S. Application Data

(63) Continuation of application No. 15/171,716, filed on Jun. 2, 2016, now Pat. No. 10,521,562.

(51) Int. Cl.
*B65G 1/137* (2006.01)
*G06F 19/00* (2018.01)
(Continued)

(52) U.S. Cl.
CPC ....... *G06F 19/3462* (2013.01); *B65G 1/0407* (2013.01); *B65G 1/08* (2013.01);
(Continued)

(58) Field of Classification Search
CPC combination set(s) only.
See application file for complete search history.

(56) References Cited

U.S. PATENT DOCUMENTS 5,208,762 A * 5/1993 Charhut ................ A61J 7/0084
                                                            221/9
5,759,009 A    6/1998 Tanaka
(Continued)

FOREIGN PATENT DOCUMENTS

DE         68928331 T2    1/1998
DE      202006002506 U1    5/2006
(Continued)

OTHER PUBLICATIONS

Translation of International Preliminary Report on Patentability for Application No. PCT/EP2017/061179, dated Dec. 4, 2018, 11 pages.
(Continued)

*Primary Examiner* — Kyle O Logan
(74) *Attorney, Agent, or Firm* — Morgan, Lewis & Bockius LLP

(57) ABSTRACT

An automatic picking machine for pharmaceutical drug packages includes at least one storage rack, at least one storage and retrieval machine, a control apparatus for controlling the storage and retrieval machine, and a filling apparatus for successively filling each of a plurality of transport containers with a group of pharmaceutical drug packages corresponding to one order, wherein the filling apparatus includes a plurality of collection containers, first transport apparatuses, each having a transport channel for conveying the pharmaceutical drug packages towards the respective collection container, and a receiving apparatus for receiving a transport container to be filled at a filling location of the filing apparatus.

20 Claims, 2 Drawing Sheets

(51) Int. Cl.
 *B65G 1/08* (2006.01)
 *B65G 1/04* (2006.01)
 *G16H 20/13* (2018.01)

(52) U.S. Cl.
 CPC ........... *B65G 1/1373* (2013.01); *G16H 20/13* (2018.01); *B65G 2201/027* (2013.01)

(56) References Cited

U.S. PATENT DOCUMENTS

| | | | | |
|---|---|---|---|---|
| RE40,510 E | * | 9/2008 | Lasher | B65B 61/20 53/55 |
| RE42,730 E | | 9/2011 | Lasher | |
| 2004/0065053 A1 | * | 4/2004 | Rice | B65B 61/20 53/445 |
| 2005/0021173 A1 | * | 1/2005 | Pinney | G07F 11/70 700/231 |
| 2007/0270998 A1 | * | 11/2007 | Luciano, Jr. | A61J 7/0069 700/216 |
| 2008/0264967 A1 | * | 10/2008 | Schifman | G07F 17/0092 221/133 |
| 2010/0089941 A1 | * | 4/2010 | Connier | B65G 1/1376 221/123 |
| 2010/0095635 A1 | * | 4/2010 | Ishiwatari | G07F 11/62 53/131.2 |
| 2010/0287880 A1 | * | 11/2010 | Yasunaga | B65B 5/103 53/64 |
| 2010/0300041 A1 | * | 12/2010 | Kim | G07F 17/0092 53/281 |
| 2011/0173926 A1 | * | 7/2011 | Yuyama | G07F 11/16 53/167 |
| 2014/0094960 A1 | * | 4/2014 | Holmes | G06F 19/3462 700/216 |
| 2014/0316556 A1 | * | 10/2014 | Hellenbrand | B65G 1/0407 700/216 |
| 2014/0377050 A1 | * | 12/2014 | Hellenbrand | B65G 1/04 414/807 |
| 2015/0274422 A1 | * | 10/2015 | Hellenbrand | B65G 47/04 414/273 |
| 2016/0114925 A1 | * | 4/2016 | Yuyama | B65B 57/16 382/141 |

FOREIGN PATENT DOCUMENTS

| | | |
|---|---|---|
| EP | 0705775 A2 | 4/1996 |
| EP | 1820754 A2 | 8/2007 |
| EP | 2719641 B1 | 10/2012 |
| EP | 2769935 A1 | 2/2013 |
| JP | S49108774 A | 10/1974 |
| WO | WO-9918014 A2 | 4/1999 |

OTHER PUBLICATIONS

European Search Report issued in EP 16 17 2596 dated Dec. 13, 2016 (12 pages).

\* cited by examiner

AUTOMATIC PICKING MACHINE FOR FILLING A TRANSPORT CONTAINER

CROSS REFERENCE TO RELATED APPLICATIONS

This application is a continuation application of U.S. application Ser. No. 15/171,716, entitled "AUTOMATIC PICKING MACHINE FOR FILLING A TRANSPORT CONTAINER," filed on Jun. 2, 2016, the entirety of which is incorporated herein by reference.

BACKGROUND

Many automatic picking machines include parallel rows of storage racks, each rack having storage surfaces on storage shelves arranged horizontally, wherein a lane is formed between the first and second rows of storage racks and between the third and fourth rows of storage racks. Each lane has a plurality of storage and retrieval machines that can travel along the lanes for storing pharmaceutical drug packages in storage sites on the storage shelves and for removing said pharmaceutical drug packages from the storage shelves. A plurality of conveyor belts extends over the entire area of the rows of racks between the second and third rows of storage racks. A plurality of reach-through windows and chutes are arranged in the second and third rows of storage racks and distributed over the length of the rows, such that the storage and retrieval machines moving in the lanes can dispense the pharmaceutical drug packages through the windows onto the chutes so that each pharmaceutical drug package thereby dispensed can reach one of the conveyor belts.

The conveyor belts transport these pharmaceutical drug packages to a front side of the four rows of shelves and further to a dispensing apparatus having a plurality of chutes, each of which enables the pharmaceutical drug packages arriving on the conveyor belts to drop into a transport container, or receptacle, arranged at a filling site. Barrier apparatuses, which prevent certain movements of the pharmaceutical drug packages arriving on the moving conveyor belt, are arranged before the end of each conveyor belt at the dispensing apparatus such that groups of pharmaceutical drug packages accumulate at these barrier devices. A control unit releases the barrier apparatus when all pharmaceutical drug packages of a single order have been collected and a transport container is ready to receive this group of packages at the dispensing apparatus. The group is then conveyed further and finally lands in the correct transport container.

SUMMARY

Many automatic picking machines include complex designs and controls of the conveyance and barrier apparatuses. Barrier apparatuses, in particular those which stop a stream of incoming pharmaceutical drug packages on a particular point along a conveyor belt, may require extensive maintenance to reliably prevent jamming of piled-up pharmaceutical drug packages. Accordingly, a need exists for an improved method and apparatus for successively filling a plurality of transport containers with a group of pharmaceutical drug packages corresponding to one order.

The present disclosure relates to an automatic picking machine for pharmaceutical drug packages. The automatic picking machine may include at least one storage rack, at least one storage and retrieval machine for storing pharmaceutical drug packages in storage sites on storage surfaces of the storage rack and for removing these pharmaceutical drug packages from said storage surfaces, a control apparatus for controlling the storage and retrieval machine and a filling apparatus for filling a plurality of transport containers in succession. Each transport container may hold a group of pharmaceutical drug packages corresponding to one order.

One or more disclosed embodiments provide an automatic picking machine for pharmaceutical drug packages. The apparatus includes, at least one storage rack and at least one storage and retrieval machine that moves in a lane in front of the at least one storage rack for storing pharmaceutical drug packages in storage sites on storage surfaces of the at least one storage rack and for removing the pharmaceutical drug packages from the storage surfaces. The method also includes a control apparatus for controlling the storage and retrieval machine, and a filling apparatus for successively filling each of a plurality of transport containers with a group of pharmaceutical drug packages corresponding to one order. The filling apparatus includes: a plurality of collection containers, each collecting one group of pharmaceutical drug packages corresponding to one order and each of the plurality of collection containers including an unloading apparatus for unloading the pharmaceutical drug packages previously collected in the collection containers at a same time, first transport apparatuses, each having a transport channel extending into the lane in an access region of the at least one storage and retrieval machine, the storage and retrieval machine being capable of dispensing pharmaceutical drug packages into a respective transport channel, and the respective transport channel conveys the pharmaceutical drug packages towards a respective collection container, wherein a first transport apparatus is assigned to each collection container, and the filling apparatus further includes a receiving apparatus for receiving a transport container to be filled at a filling location of the filing apparatus, wherein the transport container to be filled is arranged at the filling location such that the pharmaceutical drug packages unloaded by the unloading apparatus are directed into the transport container.

One or more disclosed embodiments provide an automatic picking machine for pharmaceutical drug packages. The automatic picking machine includes at least one storage rack, at least one storage and retrieval machine for storing pharmaceutical drug packages in storage sites on storage surfaces of the at least one storage rack and for removing the pharmaceutical drug packages from the storage surfaces, and a control apparatus for controlling the storage and retrieval machine. The apparatus also includes a filling apparatus for successively filling each of a plurality of transport containers with a group of pharmaceutical drug packages corresponding to one order, the group of pharmaceutical drug packages corresponding to one order having previously been collected in a collection container, wherein the filling apparatus includes a receiving apparatus for receiving a transport container to be filled at a filling location of the filing apparatus, and wherein a second transport apparatus, which conveys pharmaceutical drug packages from each of the collection container and a second collection container to the transport container, includes a separate transport apparatus for each of the collection containers.

One or more disclosed embodiments provide a method for automatically picking pharmaceutical drug packages. The method includes providing at least one storage rack, and controlling, by a control apparatus, a storage and retrieval machine that moves in a lane in front of the at least one storage rack, wherein the storage and retrieval machine stores pharmaceutical drug packages in storage sites on storage surfaces of the at least one storage rack and removes the pharmaceutical drug packages from the storage surfaces. The method also includes successively filling, by a filling apparatus, each of a plurality of transport containers with a group of pharmaceutical drug packages corresponding to one order by: collecting, by a collection container, one group of pharmaceutical drug packages corresponding to one order, unloading, by an unloading apparatus, the one group of pharmaceutical drug packages corresponding to one order collected in the collection container, conveying the one group of pharmaceutical drug packages corresponding to one order toward the collection container by a transport channel included in a first transport apparatus, the transport channel extending into the lane in an access region of the at least one storage and retrieval machine, and receiving a transport container to be filled at a filling location of the filling apparatus, by a receiving apparatus for receiving a transport container to be filled, wherein the transport container to be filled is disposed at the filling location such that the pharmaceutical drug packages unloaded by the unloading apparatus are directed into the transport container to be filled.

BRIEF DESCRIPTION OF THE DRAWINGS

The device according to the present disclosure and the method according to the present disclosure are described in greater detail below, with reference to the appended drawings, wherein.

DETAILED DESCRIPTION

Figure 1:
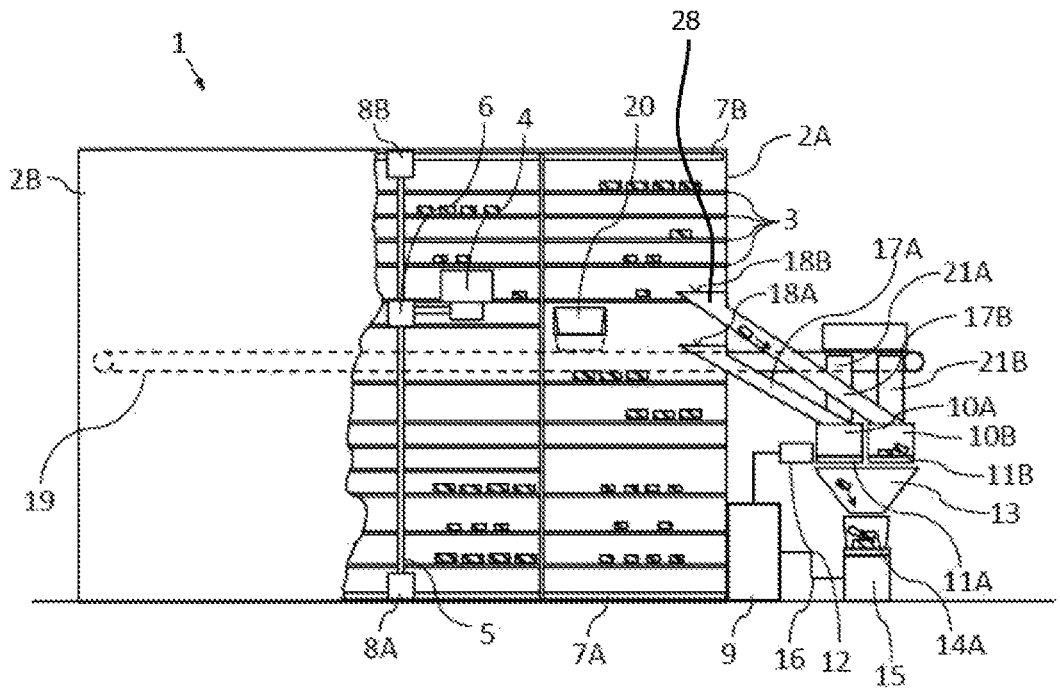
FIG. 1 is a schematic side view of an automatic picking machine according to an exemplary embodiment of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions are provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

An automatic picking machine for pharmaceutical drug packages, according to the present disclosure, may comprise at least one storage rack and at least one storage and retrieval machine. The storage and retrieval machine may be capable of moving in a lane in front of, or adjacent to, a shelf for storing pharmaceutical drug packages in storage sites disposed on storage surfaces of the storage rack and for removing these pharmaceutical drug packages from the storage surfaces. The phrase "storage rack," as used herein, should be understood to refer not only to a stationary rack having a plurality of horizontal shelves arranged one above the other, but may also refer to a stationary rack having storage shafts on inclined shelves, a stationary rack having drawers arranged one above the other such that the drawers can be pulled out of the shelf, and/or a movable sliding rack with storage shafts or individual storage sites. When employed in conjunction with movable shelves, the lanes may be of variable arrangements and dimensions. Two rows of storage shelves may be arranged in parallel so that a lane is formed between two storage shelves. The storage shelves may have flat horizontal racks on which the pharmaceutical drug packages are stored in virtual channels, which may be arranged side by side in a longitudinal or lateral direction of the rack. The storage and retrieval machine may include a storage surface for receiving one or more pharmaceutical drug packages and a gripping apparatus for moving the pharmaceutical drug packages from the storage area to a shelf or from a shelf to the storage area.

The automatic picking machine for pharmaceutical drug packages may also comprise a control apparatus for controlling the storage and retrieval machine and a filling apparatus for filling a plurality of transport containers with a group of pharmaceutical drug packages corresponding to one order in succession. The transport containers may be open boxes. The filling apparatus may include a plurality of collection containers, and each of the collection containers may be able to receive a group of pharmaceutical drug packages corresponding to one order, and the filling apparatus may further have an unloading apparatus by which the pharmaceutical drug packages collected in the collection container may be unloaded simultaneously. The filling apparatus may also include one or more first transport apparatuses, each including a transport channel extending into the lane in an access region of the at least one storage and retrieval machine. The storage and retrieval machine may dispense pharmaceutical drug packages into the transport channel, which then conveys the pharmaceutical drug packages to a respective collection container. One or more first transport apparatuses may be assigned to each collection container and one or more collection container may be assigned to each first transport apparatus. Further, each collection container may have a single first transport apparatus assigned to the collection container, and the single first transport apparatus may be assigned only to the respective collection container. The filling apparatus may also include a receiving apparatus for receiving a transport container to be filled at a filling location of the filling apparatus, wherein the transport container to be filled may be arranged at the filling location such that the pharmaceutical drug packages unloaded by the unloading apparatus are sent to the transport container.

The automatic picking machine for pharmaceutical drug packages according to the disclosure enables the collection of a group of pharmaceutical drug packages corresponding to one order in the collection containers and enables rapidly transporting said group of pharmaceutical drug packages further into a desired transport container as soon as the desired transport container is ready at the filling location.

In one embodiment, the collection containers are unloaded by simply tipping them with an unloading device. However, the collection containers may be arranged in stationary positions in one location and each collection container may have an opening on a bottom of the collection container. Each unloading apparatus may have a closure apparatus, or closing device, for closing and releasing the opening. In one embodiment, the closing devices each include a sliding roller shutter for closing and releasing the opening. The sliding roller shutters may be controlled by an electric drive or by a pneumatic drive.

In another embodiment, at least one second transport apparatus is provided for receiving the unloaded and collected pharmaceutical drug packages of the group from a collection container and for further conveying the unloaded pharmaceutical drug packages of the group to the transport container positioned at the filling location. Such an arrangement permits greater flexibility in apparatus structural design, and in the arrangement of the filling location.

In another embodiment, the second transport apparatus comprises a separate transport apparatus, for example a chute and/or a conveyor belt, for each of the collection containers. The at least one second transport apparatus may comprise a funnel-shaped guide channel with an upper opening and a lower opening, wherein the upper opening is disposed beneath one of the collection container openings on their respective bottom sides, and the lower opening may be arranged above a transport container with an open top and positioned at a filling location. A single funnel-shaped guide channel presents a simple design, wherein at a given time only one collection container is to be emptied into a transport container arranged at a filling location.

In a further embodiment, the funnel-shaped guide channel of the second transport apparatus includes a barrier apparatus, such that the pharmaceutical drug packages of one group unloaded from a collection container into the guide channel are stored temporarily upstream from, and/or by, the barrier device and can be conveyed further downstream after the barrier device is released. The contents unloaded from the collection container can thus be stored temporarily until the transport container is ready for receiving packages at the filling location. This embodiment permits intermediate buffer storage of the contents of a collection container, such that it is possible to reload the same collection container before the previously collected contents have been transferred to the transport container. The barrier apparatus may also have a sliding shutter or a rolling shutter for closing and releasing the lower opening of the guide channel.

In another embodiment, the collection containers are hoppers that are open at their tops. This allows the pharmaceutical drug packages that have been collected to be fed via the conveyor belts and also via simple chutes, whose dispensing ends may be arranged above one of the hoppers. A plurality of belts and/or chutes may be guided to, and unload into, the tops of the hoppers. The transport channel of each of the first transport apparatuses may be formed by a chute on which the pharmaceutical drug packages, which are deposited by the storage and retrieval machine at an upper end of the chute, can slide into a respective collection container. This permits a simple and reliable design. The chutes, which may include transport channels, may be arranged in parallel, one above the other, and/or side by side. In another embodiment, storage shelves are arranged parallel to longitudinal sides of the lane, or a perpendicular to an end wall, and the upper ends of the chutes of the first conveyor apparatuses are disposed on, or along, an end face of the lane. The collection containers may be disposed beyond, or outside of, the lane and in front of an end wall arranged on a front side of the lane. In other words, the collection containers may be arranged on an opposite side of the front wall than is the lane.

In another embodiment, at least one conveyor belt connected to the control apparatus is arranged between the storage surfaces of one or both storage shelves arranged in parallel to the lane and/or beside the storage shelves on a storage shelf side opposite the storage shelf side adjacent to the lane. The conveyor belt conveys the pharmaceutical drug packages placed thereon beyond the end wall, and one or more chutes may be provided, each chute having an upper end and a lower end. The upper end of each chute extends into the access region of the storage and retrieval machine in such a way that the storage and retrieval machine may deposit the pharmaceutical drug packages in the chutes. The lower end of each chute is arranged above the conveyor belt, and third transport apparatuses coupled to the control apparatus may be provided to receive the pharmaceutical drug packages from the at least one conveyor belt and to deliver the pharmaceutical drug packages into a collection container selected by the control apparatus. Such an arrangement creates one or more conveyor pathways in addition to the first transport apparatuses and permits a reduction in the distance traveled by the storage and retrieval machine, thus resulting in faster filling of the collection containers. This embodiment is particularly advantageous when used with an automatic picking machine having two or more storage and retrieval machines capable of moving in a lane.

In another embodiment, a receiving apparatus for receiving a transport container to be filled at the filling location of the filling apparatus is part of an apparatus for supplying the transport containers to be filled in succession to the filling location of a filling apparatus. This permits automation of the feed of the transport containers to be filled, and in particular permits control of the feed by the control apparatus of the automatic picking machine.

In another embodiment, two to six collection containers are provided and are arranged side by side. This range of numbers of collection containers may represent an optimum between adequate buffer capacity and structural and control complexity.

Figure 2:
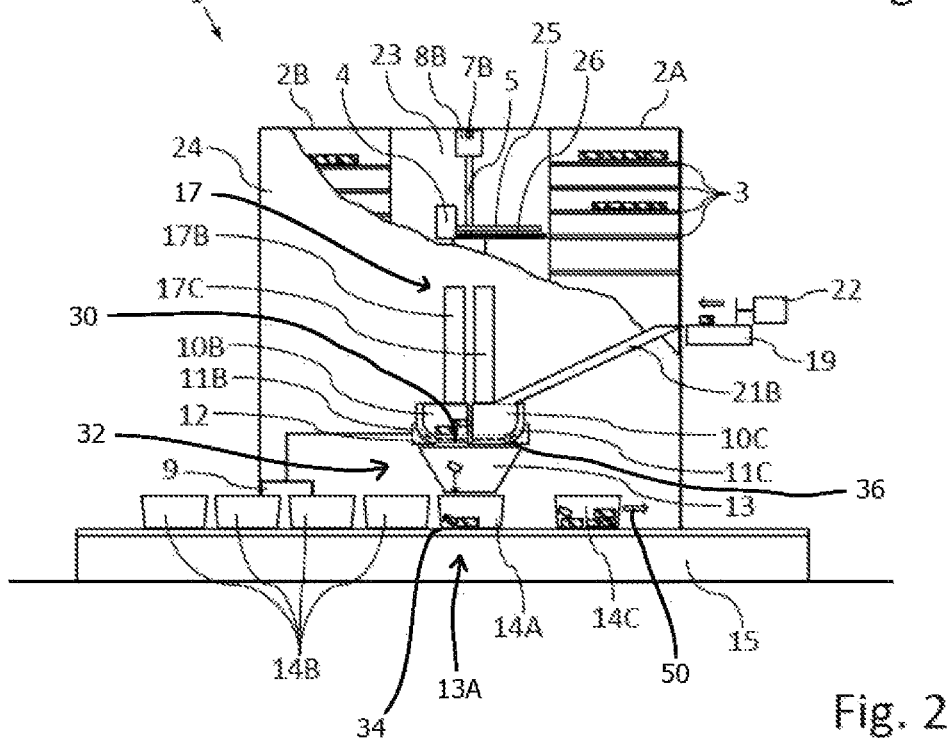
FIG. 2 is a schematic front view of the automatic picking machine of FIG. 1.

FIG. 1 is a schematic side view of an automatic picking machine 1 according to an exemplary embodiment of the present disclosure and FIG. 2 shows a schematic front view of the automatic picking machine 1 of FIG. 1. The automatic picking machine 1 may have two parallel rows of storage racks 2A, 2B forming a lane 23 therebetween. In FIG. 1, the row of racks 2B is shown in a partially cut-away diagram to expose a view into the lane 23 and into the inside of the rear row of racks 2A. The racks of the row of racks 2A and 2B may have horizontal flat shelves 3, on which pharmaceutical drug packages of various sizes and with various contents are stored without regard to a particular order, the packages being arranged side by side and one after the other in virtual channels with a distance between them.

A storage and retrieval machine 4 may move in the lane 23. In other exemplary embodiments, a plurality of storage and retrieval machines 4 may also be capable of traversing the lane 23. The storage and retrieval machine 4 may be mounted on a vertical rail 5 by a holder 6, wherein the holder 6 may have a drive for vertical movement of the storage and retrieval machine 4. The vertical rail 5 may be in turn guided on a lower rail 7A and/or an upper rail 7B by a lower guide 8A and an upper guide 8B. In this way, the storage and retrieval machine 4 may be moved vertically and horizontally in the lane 23 adjacent to, or in front of, a front side, or another side, of the rows of racks 2A and 2B disposed opposite one another and/or closest to the lane 23. The storage and retrieval machine 4 may have a gripper apparatus 25, which may comprise gripper jaws combined with slide grippers or suction pads, and a support table 26. Using the gripper jaws of the gripping apparatus 25 and/or the slide grippers and/or the suction pads guided by the gripping jaws of the gripping apparatus 25, pharmaceutical drug packages placed on a support table 26 may be pushed onto one of the flat shelves 3 if the support table 26 is positioned in front of, or adjacent to, the shelf 3. Conversely, pharmaceutical drug packages lying on the shelf 3 can be gripped using gripping jaws and/or a suction pad of the gripping apparatus 25 and pulled onto the support table 26 of the storage and retrieval machine 4.

The storage and retrieval machine 4 may be designed so that the support table 26 with the gripping jaws of the gripping apparatus 25 arranged above the support table 26 can be rotated about a vertical axis in such a way that the gripping apparatus 25 can access both rows of racks 2A and 2B. The support table 26 and the gripping apparatus 25 of the storage and retrieval machine 4 may be rotated not only by 180° for accessing the rows of racks 2A and 2B opposite one another, but also by 90° so that the storage and retrieval machine 4 can also access a front side of the lane 23.

On a front face of the lane 23, which may form the front side, there may exist a front wall 24, which is shown as partially cut-away in FIG. 2 to expose the rows of racks 2A, 2B and the lane 23 with the storage and retrieval machine 4 arranged behind the wall 24.

The storage and retrieval machine 4 may be coupled to a control apparatus 9, from where control signals and a power supply to the storage and retrieval machine 4 may be carried to the storage and retrieval machine 4 along the bottom rails 7A and along the vertical rail 5. The control apparatus 9 may comprise a computer with a processor and memory devices, as well as input and output devices for a user, such as a keyboard, a display screen and a barcode scanner.

Not shown in FIGS. 1 and 2 are devices by which new pharmaceutical drug packages to be stored are sent to the automatic picking machine for pharmaceutical drug packages 1. These devices may include a storage conveyor belt running between two shelves 3 of one of the two rows of racks 2A or 2B over an entire, or partial, length of the row of racks 2A or 2B and emerging to the outside at an end face of the row 2A or 2B. A support station, where an operator scans a pharmaceutical drug package to be entered into storage to identify the package and then places the package in a certain orientation on the storage conveyor belt, may be situated on an outgoing section of the storage conveyor belt.

In alternative embodiments, apparatuses for fully automatic storage of a larger quantity of different pharmaceutical drug packages may be provided. For example, these apparatuses may receive an entire shipment from a wholesale dealer in a receiving hopper, and automatically sort the pharmaceutical drug packages from the shipment. Further, these apparatuses may scan, and/or identify, the packages and send them to be deposited within an access range of the storage and retrieval machine 4, such that the storage and retrieval machine 4 is able to bring the new packages to a certain storage site on the shelves 3.

The automatic picking machine 1 may serve to successively fill transport containers 14A, 14B, 14C. These transport containers receive, for example, a group of pharmaceutical drug packages corresponding to one order. These orders may include a large quantity of different pharmaceutical drug packages, such as those for covering the daily needs of a ward in a hospital. The transport containers 14A, 14B, 14C may be crates that are open at their tops and may also be closed with a suitable cover after being filled. The transport containers 14A, 14B, 14C may be sent by a transport apparatus 15 to a filling location 13A, where a filling apparatus 32 of the automatic picking machine 1 facilitates automatic filling of the transport container 14A. The transport apparatus 15 comprises, for example, conveyor belts and/or rolling conveyors having suitable drives controlled by the control apparatus 9 of the automatic picking machine 1. Such an arrangement is illustrated in FIG. 1 by the schematically diagramed control lines 16 between the control apparatus 9 and the transport apparatus 15.

The embodiment shown in FIG. 2 shows a transport container 14A which is situated at the filling location 13A of the filling apparatus 32. The transport container 14C has already been filled and may be conveyed further in the direction of the arrow 50. Transport containers 14B that have yet to be filled are standing ready on the transport apparatus 15.

The filling apparatus 32 illustrated in FIGS. 1 and 2 comprises collection containers 10A-10C, of which FIG. 1 shows collection containers 10A and 10B and FIG. 2 shows collection containers 10B and 10C. Each collection container 10A-10C may hold a group of pharmaceutical drug packages corresponding to one order. Each collection container 10A-10C may have an unloading apparatus 36, by which all pharmaceutical drug packages previously collected in the collection containers 10A-10C can be unloaded at a same time. Each collection container 10A-10C may have an opening 30 on its bottom, which may be closed by a closure apparatus 11A, 11B, 11C. FIG. 2 illustrates each closure apparatus 11A-11C comprising a sliding drawer. The sliding drawers may be in a curved guide adjacent to the bottom surface and an outer side wall of the collection container 10A-10C. A drive 12, represented schematically as a box, for the four sliding drawers may be coupled to the control apparatus 9. The drive 12 may include hydraulic or pneumatic actuating drives with respective control circuits for coupling the drive 12 with the control apparatus 9. The control apparatus 9 enables a collection container 10A-10C, which is filled with a group of pharmaceutical drug packages corresponding to one order, to be emptied by sliding the sliding drawing and releasing the opening 30 at the collection container bottom. Thereafter, the packages contained in the collection container 10A-10C may be guided by a second transport apparatus 13, which may comprise a funnel-shaped guide, into a transport container 14A that is open at its top and arranged beneath the second transport apparatus 13. After a collection container 10A-10C has been emptied, the transport container 14A, filled with its contents, may be further conveyed and the next transport container 14B to be filled may be moved to the filling location 13A.

The collection containers 10A-10C may be hoppers which are open at their tops and to which the pharmaceutical drug packages that are to be collected are supplied by first transport apparatuses 17. These first transport apparatuses 17 may each have a transport channel 28 extending into the lane 23, into which the storage and retrieval machine 4 can dispense pharmaceutical drug packages, and the transport channel 28 may convey the pharmaceutical drug packages towards a respective collection container 10A-10C. The first transport apparatuses 17 of the embodiment illustrated in FIGS. 1 and 2 may be inclined chutes or shafts 17A, 17B, 17C. These inclined shafts 17A-17C lead from a receiving opening 18A, 18B, which is open at the top inside the lane 23 in the interior of the automatic picking machine 1 through a front wall 24 to a dispensing site above the respective collection container 10A-10C that is open at its top. The receiving openings 18A, 18B of the chutes or shafts 17A-17C may be arranged in the lane in such a way that the storage and retrieval machine 4 can deliver one or more packages into these receiving openings 18A, 18B at the same time, such that the packages can then slide into the collection container 10A-10C. Providing one chute 17A-17C for each collection container 10A-10C enables controlling the storage and retrieval machine 4 so as to supply pharmaceutical drug packages alternately to each one of the collection containers 10A-10C. The collection containers 10A-10C need not be filled in succession. The sequence of filling the pharmaceutical drug packages into the collection containers 10A-10C can instead be optimized as a function of the respective storage site of the pharmaceutical drug packages in the racks 2A, 2B and the required distance of travel of the storage and retrieval machine 4 so that the conveyance pathways are minimized. This aids in rapidly filling the collection containers 10A-10C.

To achieve further optimization of the transport distances, a cantilevered conveyor belt 19 may be provided, as illustrated in FIGS. 1 and 2. The cantilevered conveyor belt 19 may extend next to the row of racks 2A on a side facing away from the lane 23 in an exemplary embodiment. Furthermore, windows 20 may be provided in the outside wall of the row of racks 2A, the outside wall being connected to a chute leading to the conveyor belt 19. Storage and retrieval machine 4 can dispense pharmaceutical drug packages that the storage and retrieval machine 4 has received through these windows 20, such that the packages go through the chutes onto the conveyor belt 19. FIG. 1 illustrates one such window 20, although additional windows 20 may be provided at other locations remote from the front wall 24. The windows 20 that may be provided on the end of the storage rack 2A opposite, or disposed on another wall or at another angle from, the front wall 24 may enable the storage and retrieval machine 4 to deposit packages that have been stored in a position remote from the front wall 24 onto the conveyor belt 19, such that these packages may be conveyed by the conveyor belt 19 to, or past, the front side or the front wall, where the filling apparatus 32 is located. Such conveyance may occur while the storage and retrieval machine 4 is removing additional pharmaceutical drug packages from the shelves 3 and conveying them to the receiving openings 18A, 18B. The pharmaceutical drug packages on the conveyor belt 19 may travel to, or past, the front side or the front wall, where the filling apparatus 32 is located. The conveyor belt 19 travels next to the filling apparatus 32 beyond the front wall 24. Third transport apparatus 21, which may include chutes 21A and 21B, leading to collection containers 10A-10C may be located on the front side of the conveyor belt 19. Furthermore, a sliding apparatus 22 may be coupled to the control apparatus 9 and may slide the pharmaceutical drug packages arriving on the conveyor belt 19 from the conveyor belt 19 into the chutes 21A and 21B, such that they are conveyed into the collection containers 10A-10C. Several chutes may also be provided, each chute being assigned to one of a plurality of collection containers 10A-10C.

The filling apparatus 32 may also include a receiving apparatus 34 for receiving a transport container to be filled at a filling location 13A of the filling apparatus 32, wherein the transport container 14A-14C to be filled may be arranged at the filling location 13A such that the pharmaceutical drug packages unloaded by the unloading apparatus 36 are sent to the transport container 14A-14C.

Numerous alternative embodiments are conceivable within the scope of the concepts of the disclosure. For example, the automatic picking machine 1 for pharmaceutical drug packages may also have inclined shelves with storage shafts instead of, or in addition to, flat horizontal shelves 3. The storage and retrieval machine 4 may be adapted according to the withdrawal of pharmaceutical drug packages from inclined shafts, for example, inclined buffer shafts. The storage shelves extending along both sides of a lane need not have a flat front side. The front sides may be curved in an arc or bent at an angle. In such a case, the storage and retrieval machine 4 may also be guided along the curved and/or angled lane 23. Two or more storage and retrieval machines 4 may be guided in the lane 23, such that they may use either separate or rails 7A, 7B. The control apparatus 9, shown outside of the storage rack in FIGS. 1 and 2, may also be integrated into the automatic picking machine 1 at any location.

Figure 3:
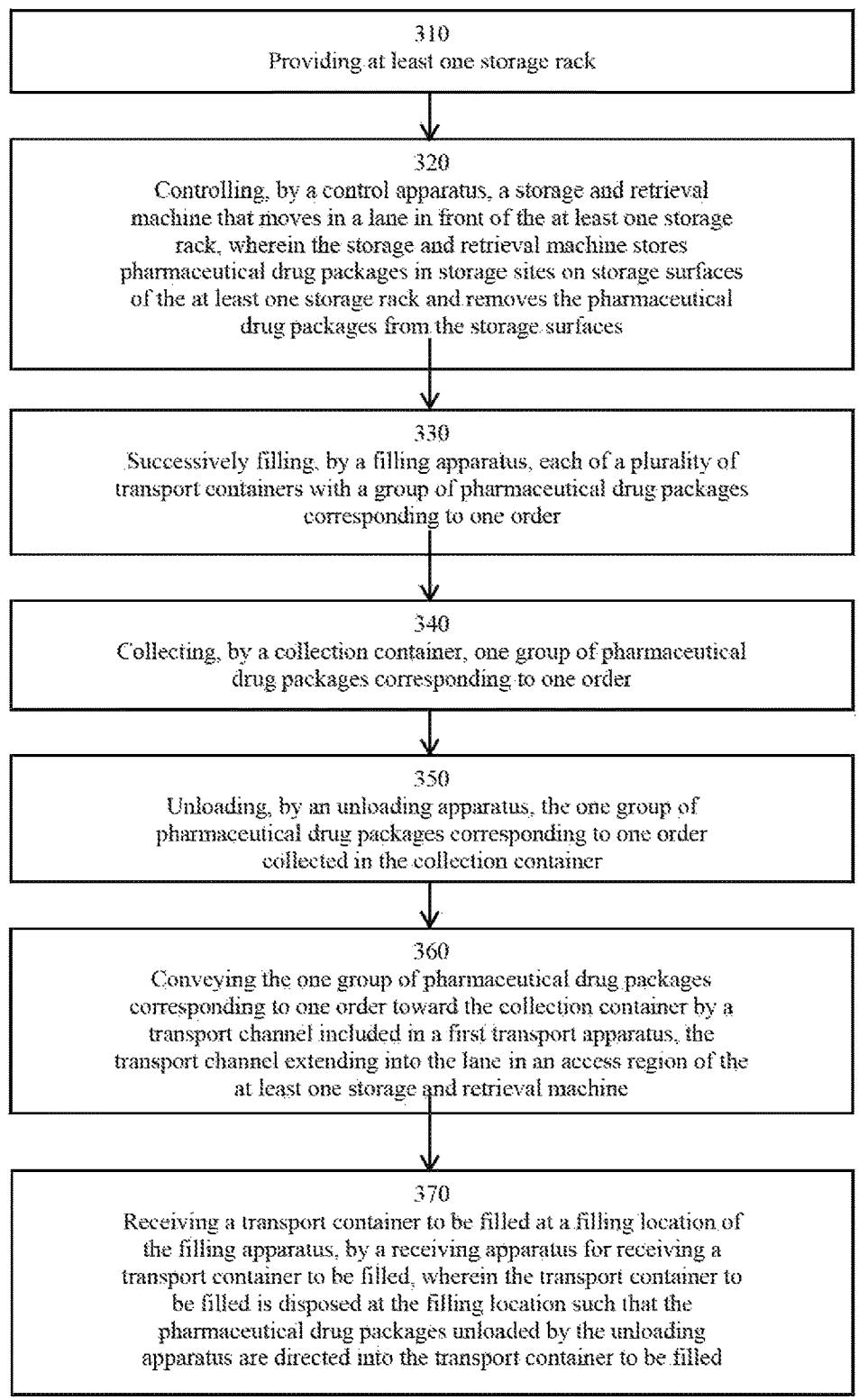
FIG. 3 is a flowchart illustrating steps in one or more embodiments of a method for automatically picking pharmaceutical drug packages.

FIG. 3 illustrates a method for automatically picking pharmaceutical drug packages 300. Step 310 includes providing at least one storage rack, and step 320 includes controlling, by a control apparatus, a storage and retrieval machine that moves in a lane in front of the at least one storage rack, wherein the storage and retrieval machine stores pharmaceutical drug packages in storage sites on storage surfaces of the at least one storage rack and removes the pharmaceutical drug packages from the storage surfaces. Step 330 includes successively filling, by a filling apparatus, each of a plurality of transport containers with a group of pharmaceutical drug packages corresponding to one order, while step 340 includes collecting, by a collection container, one group of pharmaceutical drug packages corresponding to one order. Step 350 includes unloading, by an unloading apparatus, the one group of pharmaceutical drug packages corresponding to one order collected in the collection container, and step 360 includes conveying the one group of pharmaceutical drug packages corresponding to one order toward the collection container by a transport channel included in a first transport apparatus, the transport channel extending into the lane in an access region of the at least one storage and retrieval machine. Step 370 includes receiving a transport container to be filled at a filling location of the filling apparatus, by a receiving apparatus for receiving a transport container to be filled, wherein the transport container to be filled is disposed at the filling location such that the pharmaceutical drug packages unloaded by the unloading apparatus are directed into the transport container to be filled.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject technology.

The word "exemplary" or the term "for example" is used herein to mean "serving as an example or illustration." Any aspect or design described herein as "exemplary" or "for example" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples. A phrase such an embodiment may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples. A phrase such a configuration may refer to one or more configurations and vice versa.

In one aspect, unless otherwise stated, all measurements, values, ratings, positions, magnitudes, sizes, and other specifications that are set forth in this specification, including in the claims that follow, are approximate, not exact. In one aspect, they are intended to have a reasonable range that is consistent with the functions to which they relate and with what is customary in the art to which they pertain.

It is understood that the specific order or hierarchy of steps, operations or processes disclosed is an illustration of exemplary approaches. Based upon design preferences, it is understood that the specific order or hierarchy of steps, operations or processes may be rearranged. Some of the steps, operations or processes may be performed simultaneously. Some or all of the steps, operations, or processes may be performed automatically, without the intervention of a user. The accompanying method claims, if any, present elements of the various steps, operations or processes in a sample order, and are not meant to be limited to the specific order or hierarchy presented.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112 (f) unless the element is expressly recited using the phrase "means for" or, in the case of a method claim, the element is recited using the phrase "step for." Furthermore, to the extent that the term "include," "have," or the like is used, such term is intended to be inclusive in a manner similar to the term "comprise" as "comprise" is interpreted when employed as a transitional word in a claim.

The Title, Background, Summary, Brief Description of the Drawings and Abstract of the disclosure are hereby incorporated into the disclosure and are provided as illustrative examples of the disclosure, not as restrictive descriptions. It is submitted with the understanding that they will not be used to limit the scope or meaning of the claims. In addition, in the Detailed Description, it can be seen that the description provides illustrative examples and the various features are grouped together in various embodiments for the purpose of streamlining the disclosure. This method of disclosure is not to be interpreted as reflecting an intention that the claimed subject matter requires more features than are expressly recited in each claim. Rather, as the following claims reflect, inventive subject matter lies in less than all features of a single disclosed configuration or operation. The following claims are hereby incorporated into the Detailed Description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirement of 35 U.S.C. § 101, 102, or 103, nor should they be interpreted in such a way.

The invention claimed is:

1. An automatic picking machine, comprising:
a storage and retrieval machine configured to remove drug packages from a storage rack;
at least one transport channel extending toward a delivery region from a receiving region configured to accept a respective drug package from the storage and retrieval machine;
a filling apparatus configured to receive the drug packages from the at least one transport channel at the delivery region, and configured to fill one or more transport containers with the drug packages received from the at least one transport channel as the one or more transport containers are successively moved into a filling location adjacent the filling apparatus to each receive at least a portion of the drug packages from the filling apparatus; and
a control apparatus configured to control the storage and retrieval machine, and cause the storage and retrieval machine to provide the drug packages removed from the storage rack to the at least one transport channel, and configured to cause the one or more transport containers to successively move to the filling location and be filled by the filling apparatus.

2. The automatic picking machine of claim 1, wherein the filling apparatus comprises:
a plurality of collection containers; and
one or more transport apparatuses;
wherein the control apparatus is configured to cause at least a portion of the drug packages to be received into a first collection container of the plurality of collection containers, and to cause a first transport container of the one or more transport containers to be filled from the first collection container via the one or more transport apparatuses.

3. The automatic picking machine of claim 2, wherein the filling apparatus comprises an unloading apparatus configured to cause an unloading of at least one drug package received into the first collection container to fill the first transport container.

4. The automatic picking machine of claim 2,
wherein the filling location is located below the plurality of collection containers, and
wherein a bottom of each collection container is configured to be selectively opened or closed, and when the bottom of the first collection container is opened the drug packages received into the first collection container are unloaded into the transport container positioned below the first collection container.

5. The automatic picking machine of claim 2, wherein each collection container is configured to receive drug packages from a different transport channel of a plurality of transport channels, the plurality of transport channels including the at least one transport channel.

6. The automatic picking machine of claim 2, wherein the one or more transport apparatuses comprises a first transport apparatus and a second transport apparatus,
wherein the first transport apparatus includes a funnel-shaped guide channel having an upper opening and a lower opening, wherein the upper opening is arranged beneath the opening of the first collection container, and the lower opening is arranged above the first transport container when the first transport container is at the filling location,
wherein the first transport container is configured to receive the the respective drug packages through an open top when positioned at the filling location.

7. The automatic picking machine of claim 1, wherein the storage and retrieval machine is mounted on a vertical rail, and includes a drive configured to vertically move the storage and retrieval machine, and
wherein the vertical rail is guided on one or more horizontal rails, such that the storage and retrieval machine is movable vertically and horizontally across and adjacent to a plurality of storage racks.

8. A method, comprising:
causing an automated storage and retrieval machine to remove drug packages from a storage rack;
receiving, at a filling apparatus, the drug packages from at least one transport channel, the at least one transport channel extending toward the filling apparatus from a receiving region configured to accept a respective drug package from the storage and retrieval machine;
successively moving one or more transport containers into a filling location adjacent the filling apparatus to receive at least a portion of the drug packages from the filling apparatus; and
filling the one or more transport containers with the the drug packages received from the at least one transport channel.

9. The method of claim 8, further comprising:
causing at least a portion of the drug packages to be received into a first collection container of a plurality of collection containers; and
causing a first transport container of the one or more transport containers to be filled from the first collection container via one or more transport apparatuses.

10. The method of claim 9, wherein the filling apparatus comprises an unloading apparatus configured to cause an unloading of the portion of the drug packages received into the first collection container, the method further comprising causing the unloading of the drug packages received into first collection container to fill the first transport container.

11. The method of claim 10, wherein the filling location is located below the plurality of collection containers, and wherein a bottom of each collection container is configured to be selectively opened or closed, the method further comprising:
selectively opening the bottom of the first collection container so that the drug packages received into the first collection container are unloaded into the transport container positioned below the first collection container.

12. The method of claim 11, wherein the one or more transport apparatuses comprises a first transport apparatus and a second transport apparatus,
wherein the first transport apparatus includes a funnel-shaped guide channel having an upper opening and a lower opening, wherein the upper opening is arranged beneath the opening of the first collection container, and the lower opening is arranged above the first transport container when the first transport container is at the filling location,
wherein the first transport container is configured to receive the the respective drug packages through an open top when positioned at the filling location.

13. The method of claim 11, wherein each of the plurality of collection containers holds a group of drug packages corresponding to one order, the method further comprising:
causing all of the plurality of collection containers to be unloaded at the same time.

14. The method of claim 8, further comprising:
receiving, into each collection container, drug packages from a different transport channel of a plurality of transport channels, the plurality of transport channels including the at least one transport channel.

15. The method of claim 8, wherein causing an automated storage and retrieval machine to remove drug packages from a storage rack comprises:
causing the storage and retrieval machine to move vertically and horizontally across and adjacent to a plurality of storage racks using a plurality of vertical and horizontal rails positioned adjacent to the storage racks.

16. A control apparatus configured to:
cause an automated storage and retrieval machine to remove drug packages from a storage rack;
cause a filling apparatus to receive drug packages from at least one transport channel, the at least one transport channel extending toward the filling apparatus from a receiving region configured to accept a respective drug package from the storage and retrieval machine;
successively move one or more transport containers into a filling location adjacent the filling apparatus to receive at least a portion of the drug packages from the filling apparatus; and
cause the one or more transport containers to be filled with the the drug packages received from the at least one transport channel.

17. The control apparatus of claim 16, further configured to:
cause at least a portion of the drug packages to be received into a first collection container of a plurality of collection containers; and
cause a first transport container of the one or more transport containers to be filled from the first collection container via one or more transport apparatuses.

18. The control apparatus of claim 17, wherein the filling location is located below the plurality of collection containers, and wherein a bottom of each collection container is configured to be selectively opened or closed, the control apparatus further configured to:

selectively cause the bottom of the first collection container to open so that the drug packages received into the first collection container are unloaded into the transport container positioned below the first collection container.

19. The control apparatus of claim 16, further configure to:
cause drug packages to be received into each collection container from a different transport channel of a plurality of transport channels, the plurality of transport channels including the at least one transport channel.

20. The control apparatus of claim 16, wherein the control apparatus being configured to cause an automated storage and retrieval machine to remove drug packages from a storage rack comprises comprises the control apparatus being configured to:
cause the storage and retrieval machine to move vertically and horizontally across and adjacent to a plurality of storage racks using a plurality of vertical and horizontal rails positioned adjacent to the storage racks.

\* \* \* \* \*

UNITED STATES PATENT AND TRADEMARK OFFICE
CERTIFICATE OF CORRECTION

PATENT NO. : 10,839,047 B2
APPLICATION NO. : 16/730846
DATED : November 17, 2020
INVENTOR(S) : Christoph Hellenbrand Page 1 of 1

It is certified that error appears in the above-identified patent and that said Letters Patent is hereby corrected as shown below:

In the Claims

In Column 13, Line 50:
Replace "containers with the the", with --containers with the--.

In Column 14, Line 21:
Replace "receive the the respective", with --receive the respective--.

In Column 15, Line 15:
Replace "rack comprises comprises the", with --rack comprises the--.

Signed and Sealed this
Twenty-seventh Day of April, 2021

Drew Hirshfeld
*Performing the Functions and Duties of the*
*Under Secretary of Commerce for Intellectual Property and*
*Director of the United States Patent and Trademark Office*